US006875181B2

(12) United States Patent
Kajimoto et al.

(10) Patent No.: US 6,875,181 B2
(45) Date of Patent: Apr. 5, 2005

(54) MENTATION TEST METHOD AND MENTATION TEST APPARATUS

(75) Inventors: Osami Kajimoto, Sakai (JP); Takeo Takahashi, Minoo (JP)

(73) Assignee: Kabushikigaisha Sogo Ikagaku Kenkyusyo, Osaka (JP)

( * ) Notice: Subject to any disclaimer, the term of this patent is extended or adjusted under 35 U.S.C. 154(b) by 0 days.

(21) Appl. No.: 10/656,449

(22) Filed: Sep. 4, 2003

(65) Prior Publication Data

US 2004/0059249 A1 Mar. 25, 2004

Related U.S. Application Data

(62) Division of application No. 09/813,906, filed on Mar. 21, 2001, now Pat. No. 6,648,834.

(30) Foreign Application Priority Data

Oct. 6, 2000 (JP) ........................................ 2000-307147

(51) Int. Cl.$^7$ .............................................. A61B 13/00
(52) U.S. Cl. ......................... 600/558; 600/600; 128/898
(58) Field of Search ................................ 600/300, 558; 128/897, 898; 434/112, 118, 236–238, 258, 322, 350, 362; 273/445, 454, 459–461

(56) References Cited

U.S. PATENT DOCUMENTS 6,053,739 A * 4/2000 Stewart et al. ............... 434/236
6,485,417 B1 * 11/2002 Bowles et al. ............... 600/300
6,497,576 B1 * 12/2002 Smith ........................... 434/236
6,648,834 B2 * 11/2003 Kajimoto et al. ............ 600/558

FOREIGN PATENT DOCUMENTS

| JP | 05300908 A | * | 11/1993 | ........... A61B/10/00 |
| JP | 06327659 A | * | 11/1994 | ........... A61B/5/16 |
| JP | 11-118020 A | * | 7/1999 | ........... A61B/5/16 |
| WO | WO 8901759 A1 | * | 3/1989 | ........... A61B/5/16 |
| WO | WO 9316637 A1 | * | 9/1993 | ........... A61B/5/16 |

* cited by examiner

Primary Examiner—Charles Marmor
(74) Attorney, Agent, or Firm—Jordan and Hamburg LLP

(57) ABSTRACT

A mentation test method that can test mentation of a human such as conjecture of brain's mentation age, discrimination of early stage of dementia and prediction of onset of dementia in addition to diagnosis of prediction probability of onset of dementia and screening of mental functions of senile dementia patients, decision of the effect of rehabilitation of the aftereffects of cerebrovascular disfunction, investigation of the therapeutic effects of medicines and side effects such as sleepiness, testing of degree of intoxication, testing of peripheral attention visual field, testing of cerebral dominant hemisphere, testing of various psychoneurosis such as schizophrenia and cerebrovascular disorder (syndrome and diagnosis, and decision of the effects of rehabilitation and treatment), and check of the degree of fatigue.

10 Claims, 6 Drawing Sheets

MENTATION TEST METHOD AND MENTATION TEST APPARATUS

BACKGROUND OF THE INVENTION

1. Field of the Invention

The present invention relates to a method for testing mentation of humans, and a mentation test apparatus. More specifically, the present invention relates to a highly reproducible and reliable mentation test method that is able to sensitively test human mentation without being affected by intelligence, educational carrier and the effects of repeated learning, and a mentation test apparatus.

2. Description of the Background Art

A mentation test method called TMT (Trail-Making-Test) has been used for finding diseases such as cerebrovascular disorder, schizophrenia and dementia. In this method, test subjects are given a task to sequentially line the figures of 1 to 25 randomly distributed on a sheet of A4 paper within a period as short as possible in a manner similar to one stroke drawing. While the time required for a test subject to complete the task, or to gain a score, is recognized to be affected by the intelligence quotient of the subject as well as by aging to some extent, there are different opinions on the effect of the school carrier.

Since the task can be achieved within a short period of time by simultaneously proceeding two sorts of tasks of search of a target and memory of locations of letters and figures other than the target in the TMT method, higher concurrent processing ability between recognition and retention of information (memory), or higher processing ability of the working memory, results in better results.

However, many other functions such as flexibility of mentation, attention span (fatigue), visual search ability and motor ability are required besides the working memory for achieving the task of the TMT method. Accordingly, lower performance of the aged person is conjectured as a result of age-related changes of these factors above.

However, it is impossible in the currently available TMT method to analyze what factors have affected to what extent on the decrease of the score, thereby making it impossible to assess the working memory ability of aged persons and dementia patients.

SUMMARY OF THE INVENTION

Accordingly, one object of the present invention for solving the problems in the conventional art is to provide a mentation test method capable of testing human mentation such as conjecture of brain mentation age, discrimination of initial dementia and prediction of onset thereof as well as diagnosis of onset prediction probability and screening of mentation of the senile dementia patients, decision of the rehabilitation effect on the aftereffects of the cerebrovascular dysfunction, therapeutic effects of medicines and investigation of side effects such as sleepiness, testing of intoxication, testing of peripheral attention visual field, testing of the cerebral dominant hemisphere, testing of various neuropathy and mental disorder such as schizophrenia and cerebrovascular disorder (symptoms and diagnosis), and decision of the effect of rehabilitation and treatment), and check of mental fatigue. Another object of the present invention is to provide a mentation test apparatus capable of executing the method described above.

The mentation test method according to the present invention (referred as a method according to the present invention hereinafter) for attaining the foregoing objects uses a technical method comprising displaying a given number of randomly disposed targets to be pointed in a prescribed order on a screen of a display device, measuring a search response time required for a test subject to search each target by pointing the target in a prescribed order, and calculating the test subject's mentation based on the measured values.

In a method according to the present invention, many normal test subjects are given a visual search task for pointing the targets displayed on the screen of the display device in a prescribed order to measure the search response time for each target. Consequently, the correlation between the age and score can be statistically determined, and brain's mentation age can be conjectured from the statistically determined correlation and score of each test subject.

In a different method according to the present invention, a test subject is given a task in which mnemonic ability of the test subject is reflected on reduction of the search response time, and a task in which mnemonic ability of the test subject is hardly reflected on reduction of the search response time to measure the search response time for each target. Consequently, more accurate correlation between the age and score can be statistically determined, and the brain's mentation age can be more accurately conjectured from the statistically determined correlation and score of each test subject.

In a different method according to the present invention, the test subject is given a task in which mnemonic ability of the test subject is reflected on reduction of the search response time, and a task in which mnemonic ability of the test subject is hardly reflected on reduction of the search response time to measure the search response time for each target. Consequently, processing ability of the working memory can be analyzed by calculating contraction rate of the search response time arising from the working memory.

Prediction probability of early onset of dementia or onset of dementia can be diagnosed by statistically determining the contraction rate of the search response time arising from the working memory of the normal subjects and dementia patients, and by comparing the statistically determined contraction rate of the search response time arising from the working memory with that of each test subject.

When the test subject is given a task in which mnemonic ability of the test subject is hardly reflected on reduction of the search response time in the method according to the present invention, and when the search response time is measured for each target, then the search response time for the late turns of search tends to be prolonged, besides it is further elongated as the test subject is aged.

Delay of this search time is thought to arise from fatigues, and the causes of the fatigues include intoxication, effects of medicines, side effects of medicines, asthenopia and mental fatigue.

Therefore, the correlation between the cause and achievement is statistically determined using, for example, age as a parameter for every cause or for every time when two or more of these causes compete with one another in the present invention. It is then made possible to diagnose the extent of intoxication, effects of medicines, side effects of medicines, asthenopia and mental fatigue by comparing the correlation with the score of each test subject.

The other causes of arising delay of the search response include constriction of peripheral attention visual field and loss of exercise function. The extents of constriction of peripheral attention visual field and loss of exercise function can be also diagnosed by collecting statistical data by the same method as described above, and by comparing the statistical data with the test score of each test subject.

The method according to the present invention will be described in more detail hereinafter.

While the display device comprising a screen for displaying targets is not particularly restricted so long as the display device is able to switch the display image on the screen for every response of the test subject, it is preferable that the display device can quickly switch the screen and is excellent in the degree of freedom for setting image contents.

For example, a display device like a paper picture show may be employed, whereby the device comprises a roll paper for sequentially and continuously printing the images that change for every response of the test subject, and the roll paper is wound from one end to the other end for every screen when the test subject shows a correct response. However, it is preferable to use a display device that can display the targets on the screen by electronic control that can rapidly switch the screen and is excellent in the degree of freedom in setting the contents of the images, or a display device that can display the targets on the screen by computer control.

Although the number of the targets to be displayed is limited on a sheet of paper, the computer controlled display method is able to be infinitely continued by erasing the pointed targets from the screen and creating new targets. Since the response time is gradually delayed by proceeding the search responses for pushing the points, analysis of readily occurring fatigue is possible from the degree of delay of the response time. It has been already shown that response delay phenomenon is observed at an earlier time in the patients with chronic fatigue syndrome than in normal subjects, which enables the patients with chronic fatigue syndrome to be discriminated.

The representative display device of this sort includes a cathode ray tube (CRT) display device, a liquid crystal display device and a dichromic mirror display device.

Usually, a display device available has target pointing means comprising a cursor displayed on the screen, a cursor control means for controlling the display position of the cursor in accordance with operations by the test subject, and a pointer for allowing the computer to recognize that the cursor has been positioned at the position of the target by the input operation of the test subject.

However, it is preferable that a touch panel comprising a transparent matrix switch is overlaid on the display screen so that the corresponding target is pointed when the test subject presses the position corresponding to the target on the touch panel overlaid on the screen, in order to avoid large errors from occurring a result of the skill and delay for operating the cursor and pointer by the test object.

While the targets pressed by the test subject in a correct order may be left behind on the screen in the method according to the present invention, it is preferable that the targets pointed in a correct order are erased from the screen in order to avoid misunderstanding of the pointing order and repeatedly pressing the same target.

However, the conditions for searching the targets turn out to be easier at the later order of search when the number of the targets displayed on the screen decreases by erasing the pointed targets. Consequently, the target may be so readily and promptly searched that delay due to fatigue is hardly detected.

Accordingly, dummy targets are displayed in place of the erased targets at random positions or at the position of the erased targets in the present invention, when the targets are pointed in a correct order. It is therefore desirable that the targets are searched under the same condition irrespective of the order of search, or under the conditions that the targets are searched in a correct order among the constant number of similar images displayed on the screen, in order to sharply reflect the delay of the search response time due to fatigue.

The targets as used herein is not restricted to the target to be immediately searched, but includes the targets to be searched and pointed sooner or later. The targets comprise images provided with marks representing the order of pointing, for example figures, alphabets or Japanese letters (katakana or hiragana), or images comprising the marks themselves indicating the order of pointing.

The dummy target comprises an image displayed by a similar configuration to each target, and is displayed at the position of the erased target, or at random positions. While the dummy target may have the same color, shape and size as those of the target, at least one of the color, shape and size of the dummy target may be different from those of the target for simplifying search of the target to some extent.

When the mark indicating the order of pointing is displayed as a target, or displayed in addition to the target, a mark other than the marks already displayed may be displayed as a dummy target, or may be displayed in addition to the dummy target, so that search operations are simplified to some extent. At least one of the color, shape and size of the target may be different from those of the dummy target, or a dummy target not attached with the mark may be displayed in place of the erased target and mark, when a mark indicating the order of pointing is displayed in addition to the target.

The display position for the target may be fixed in the present invention, or may be changed every time when the target has been pointed in a correct order. The display position for the dummy target may be also fixed, or may be changed every time when the target has been pointed in a correct order.

The search response time is contracted in descending order of search, by the parallel processing of search of a target and memory of the other targets and dummy targets, or by operating the working memory, when the display position of the target and dummy target are fixed.

The search response time is further contracted in descending order of search, particularly when at least one of the color, shape and size of the dummy target is different from those of the target for easy recognition of the decreased number of the targets.

When the display positions of a target, or the display positions of the target and a dummy target are changed every time when the target has been pointed in a correct order, on the contrary, the memory of the test subject is hardly reflected on contraction of the search response time since the memory on the target position before pointing the last target is invalid. Consequently, the search response time is prolonged by fatigue as the search order is descending.

While visual disorder such as presbyopia, cataract and glaucoma may result in delay of the search response time in the method according to the present invention, the effect of such delay can be solved by devising the size, shape and color of the target, and the background color.

It was proved in the course of development of the present invention that highly reliable calculation results are obtained by executing the test 1, test 2 and test 3 in a prescribed order, measuring the search response time required for searching the targets in each test for every targets, and calculating the mentation age of the test subject's brain based on the measured values. The contents of the test 1, test 2 and test 3 are as follows:

The test 1 comprises the steps of displaying a given number of targets to be pointed in a prescribed order by randomly distributing them on the screen of a display device, allowing a test subject to point each target in a prescribed order, and displaying a dummy target having a different color from the target at the position of the pointed target in place of the pointed target when the target is pointed in a correct order;

The test 2 comprises the steps of displaying a given number of targets to be pointed in a prescribed order by randomly distributing them on the screen of a display device, allowing a test subject to point each target in a prescribed order, and displaying a dummy target at random positions in place of the pointed target when the target is pointed in a correct order; and The test 3 comprises the steps of displaying a given number of targets to be pointed in a prescribed order by randomly distributing them on the screen of a display device, allowing a test subject to point each target in a prescribed order, and displaying a dummy target at random positions in place of the pointed target when the target is pointed in a correct order, besides changing the display positions of each target and dummy target.

The number of the targets displayed is not particularly restricted, but 25 targets may be initially displayed as in the conventional TMT method.

It is preferable to disregard the search response times corresponding to the targets from the first to a prescribed order, for example from the first to the fifth targets, in each test from the test data considering emotional tension and the effect of unaccustomed work at the beginning of the test.

With respect to the search response times for the targets thereafter, the targets are divided into two groups of the first half targets of sixth to $15^{th}$ and last half targets of $16^{th}$ to $25^{th}$ in order to simplify the mentation test, and the mentation test is calculated based on the sum of the first half search response times and last half search response times.

The mentation age of the test subject's brain is actually calculated based on the results of the first half of the test 1, the last half of the test 2, the first half of the test 3 and the last half of the test 3, because a strong correlation with the age has been observed among the first half of the test 1 as a sum of the search response times from the sixth to the $15^{th}$ in the test 1, the last half of the test 2 as a sum of the search response times from the $16^{th}$ to the $25^{th}$ in the test 2, the first half of the test 3 as a sum of the search response times from the sixth to the $15^{th}$ in the test 3, and the last half of the test 3 as a sum of the search response times from the $16^{th}$ to the $25^{th}$ in the test 3.

Equations (regression functions) are used for the stepwise regression analysis with a regression curve correction, which are represented by the following equations 1 and 2.

Equation 1:

$$X = 0.0154 \times (\text{first half of task } A) + 0.00978 \times \\ (\text{last half of task } C) - 0.005535 \times \\ (\text{first half of task } C) + 0.003645 \times \\ (\text{last half of task } B) - 3.681 \\ (\text{distinction of sex}) - 6.612$$

The "distinction of sex" is substituted with 1 or 2 when the test subject is male or female, respectively.

Equation 2:

$$\text{ATMT calculated age } (Y) = -0.0091X^2 + 1.8771X - 19.192$$

While the mentation age of the test subjects' brain is somewhat distributed in their twenties, it is close to the actual age in their thirties or more, showing that this method is highly reliable.

The test subject may be informed of his (her) mentation state at the test site in the method according to the present invention, when the search response time in each test is displayed on the screen immediately after completing the entire tests. The test subject can enjoy the mentation test of the brain as if he (or her) is playing a game, because the test subject is able to learn his (her) mentation age of the brain at the test site when the calculated mentation age of the test subject's brain is displayed on the screen after completing the entire tests.

It was also proved in the course of development of the method according to the present invention that presence of dementia or prediction probability of onset of dementia can be decided from the calculated values obtained by executing the test 2 and the test 3 in a prescribed order, measuring the search response time required for searching each target in each test, and calculating the ratio of the search response time in the test 3 against the search response time in the test 2.

It was proved that the ratio is 0.85 or more for the dementia patients while the ratio is less than 0.85 for most of the normal subjects, when the ratio of the search response time in the test 3 against the search response time in the test 2 (the contraction ratio) is calculated.

Accordingly, presence of early stage dementia can be diagnosed whether the ratio is 0.85 or more or not. When the ratio is less than 0.85, it is possible to diagnose prediction probability of onset of dementia by the calculation result or by the percentage obtained based on the calculation result.

When the result of the diagnosis, or the ratio of the search response time of the last half of the test 3 relative to the search response time of the last half of the test 2, is 0.85 or less, the test subject can be informed of the prediction probability of onset of dementia at the test site by displaying the ratio or the percentage calculated based on the ratio after completing the entire tests as the prediction probability of onset of dementia. When the search response time for each test is displayed on the screen after completing the entire tests, the test subject can also recognize his (her) mentation state at the test site.

Of course, the test results of various mentations may be printed out with a printer, expressed as a voice output, or recorded on an appropriate recording medium.

A simple task in which the targets are pointed in a order of "1→2→3→ . . . ", "A→B→C→ . . . ", "a→b→C→ . . . " and "α→β→γ→ . . . " may be employed in the method according to the present invention. However, an optimum test tailored for the intelligence level of a test subject may be also possible by permitting the test subject to select a higher rank of task such as a combination of two or more sorts of orders (a category shift task) such as "1→a→2→b→3→c . . . " or a inverse order distracter task such as "25→24→23→ . . . " as in the TMT-B task.

Otherwise, emergence patterns and coordinates of the targets may be previously determined in the test 3 while displaying dummy targets every time at random positions, which enables cerebral dominant hemisphere and visual field disorders such as constriction of peripheral attention visual field to be tested from the previously stored coordinates of the targets (vectors) and their search response times.

The mentation test apparatus according to the present invention (referred as an apparatus according to the present invention hereinafter) for attaining the foregoing objects employs a technical method comprising: a display device for displaying images by electronic control; a transparent touch panel overlaid on the screen of the display device; an image control device for randomly displaying a given number of targets to be pointed in a prescribed order on the screen by electronic control of the display device, and for erasing the targets that have been pointed in a correct order when a test subject have pointed the targets by pressing the positions on the touch panel corresponding to each target in a prescribed order; a time counter for measuring the search response time required for the test subject to search the targets in a correct order and/or the search response time required for the test subject to search a given number of the targets in a continuous order; and a processing unit for calculating the test subject's mentation based on the search response time measured with the time counter.

In the method described above, a given number of the targets to be pointed in a prescribed order are displayed on the screen by being randomly distributed, the search response time required for the test subject to search each target is measured by allowing the test subject to point each target in a prescribed order, and the mentation of the test subject is calculated based on the measured values.

Detailed description of the method according to the present invention is omitted herein in order to avoid repeated explanations, since the display device has been described in the section of the detailed description of the invention.

The touch panel comprises, as is now in the art; a matrix of a number of switching elements using a transparent electrode. The display positions are transferred into the image control device as coordinates when the switching element corresponding to each target on the screen is pressed.

The image control device is provided with a function for allowing a given number of the targets to display on the screen of the display device by randomly distributing them.

Actually, the image control device comprises, for example, a data base that stores an initial display panel table in which the coordinates of a given number of the targets displayed on the initially displayed screen (initial screen) are recorded, and a main unit for controlling the display device based on the read-out data from this data base and input data from the touch panel.

Consequently, the main unit reads the disposition (emergence pattern) of the targets and dummy targets displayed on the screen from the data base, and controls the display device to display the targets and dummy targets on the screen.

Although the display positions of the targets have been previously determined as coordinates in this emergence pattern, the display position of each target is actually determined so that each target is displayed at random positions on the screen.

The image control device is also provided with a function for halting display of the corresponding targets when the main unit reads a coordinate of a switching element pressed through the touch panel, and when the coordinate coincides with the coordinate of a correct target, and a function for erasing the corresponding target from the screen.

The image control device allows the display device to display the dummy target at the position of the erased target or at random positions in place of the erased target, in order to maintain the condition that the targets are searched in a correct order among a given number of resembling targets displayed on the screen.

The data with regard to the color, shape, size and display position of the dummy target may be stored, for example, in the data base.

When the image control device permits the display device to display a mark indicating the order of pointing as a target, the display device displays a mark other than the mark that has been already displayed at the position of the erased target or at random positions in place of the erased target, in order to prevent misunderstanding of the pointing order or repeated pressing.

When the figures of 1 to 25 are displayed as the targets, for example, the figure of "26" is displayed at the position where the figure "1" has been displayed or at random positions as a dummy target in place of the figure "1" when the figure "1" has been pointed and erased from the screen. Likewise, when the image control device allows the display device to display a mark indicating the order of pointing in addition to the target, the display device displays a dummy target together with a mark other than the mark that has been already displayed at the position of the erased target or at random positions in place of the erased target, in order to prevent misunderstanding of the pointing order or repeated pressing.

While an image comprising the same color, shape and size as those of the target may be used as the dummy target, the image control device may permit the display device to display a dummy target in which at least one of the color, shape and size is different from those of the erased target, thereby enabling the range of the search area of the remaining targets to be narrowed and the search response time to be contracted.

The data base may be made to store the emergence pattern of the targets before the targets are pointed and the emergence pattern of the remaining targets and dummy targets after each target has been pointed, besides making the display position of each target in each emergence pattern to be different to one another. As such, the image control device reads the emergence pattern of the remaining targets and dummy targets after the targets have been pointed every time when the targets have been pointed in a correct order, or allows the display device to display each target that has not been pointed yet and dummy target by changing their display positions.

When the image control device comprises a function for permitting the display device to display each target at a fixed position until all the targets have been sequentially pointed, a function for allowing the display device to display the remaining targets by changing their display position every time when a target has been pointed, and a selection unit for making any one of the functions effective, both tasks of the tests in which the target positions are fixed and the target positions are changed may be simultaneously executed.

For example, the tests available comprise the test 1 in which a given number of the targets to be pointed in a prescribed order are displayed on the screen of the display device by being randomly distributed, the test subject is requested to point each target in a prescribed order, and a dummy target having a different color from the pointed target is displayed at the position of the pointed target in place of the pointed target when the target has been pointed in a correct order; or the test 2 in which a given number of the targets to be pointed in a prescribed order are displayed on the screen of the display device by being randomly distributed, the test subject is requested to point each target in a prescribed order, and a dummy target is displayed at the position of the pointed target in place of the pointed target when the target has been pointed in a correct order; and the test 3 in which a given number of the targets to be pointed in a prescribed order are displayed on the screen of the display device by being randomly distributed, the test subject is requested to point each target in a prescribed order, and a dummy target is displayed at the position of the pointed target in place of the pointed target while changing the display positions of each target and dummy target when the target has been pointed in a correct order.

Three sorts of tests according to the functions below are available, when the method according to the present invention comprises a function for displaying the targets by fixing their positions until all the targets have been sequentially pointed, besides displaying a dummy target having a different color from the pointed target in place of the pointed target, a function for displaying the targets by fixing their positions until all the targets have been sequentially pointed, besides displaying a dummy target at random positions in place of the pointed target, a function for displaying the remaining targets by changing their positions every time when a target has been pointed, and a selection unit for making any one of the functions effective.

For example, the tests available comprise the test 1 in which a given number of the targets to be pointed in a prescribed order are displayed on the screen of the display device by being randomly distributed, the test subject is made to point each target in a prescribed order, and a dummy target having a different color from the pointed target is displayed at the position of the pointed target in place of the pointed target when the target has been pointed in a correct order; the test 2 in which a given number of the targets to be pointed in a prescribed order are displayed on the screen of the display device by being randomly distributed, the test subject is made to point each target in a prescribed order, and a dummy target is displayed at random positions in place of the pointed target when the target has been pointed in a correct order; and the test 3 in which a given number of the targets to be pointed in a prescribed order are displayed on the screen of the display device by being randomly distributed, the test subject is made to point each target in a prescribed order, and a dummy target is displayed at random positions in place of the pointed target while changing the display positions of each target and dummy target when the target has been pointed in a correct order.

It is of course possible to set various functions other than those described above such as a function for allowing the emergence pattern (display positions), color, shape, size and background color of the targets and dummy targets to change, by appropriately selecting the data stored in the data base and control program in the image control device.

DESCRIPTION OF THE PREFERRED EMBODIMENT

The mentation test method and mentation test apparatus in an embodiment of the present invention will be described with reference to the drawings.

Figure 1:
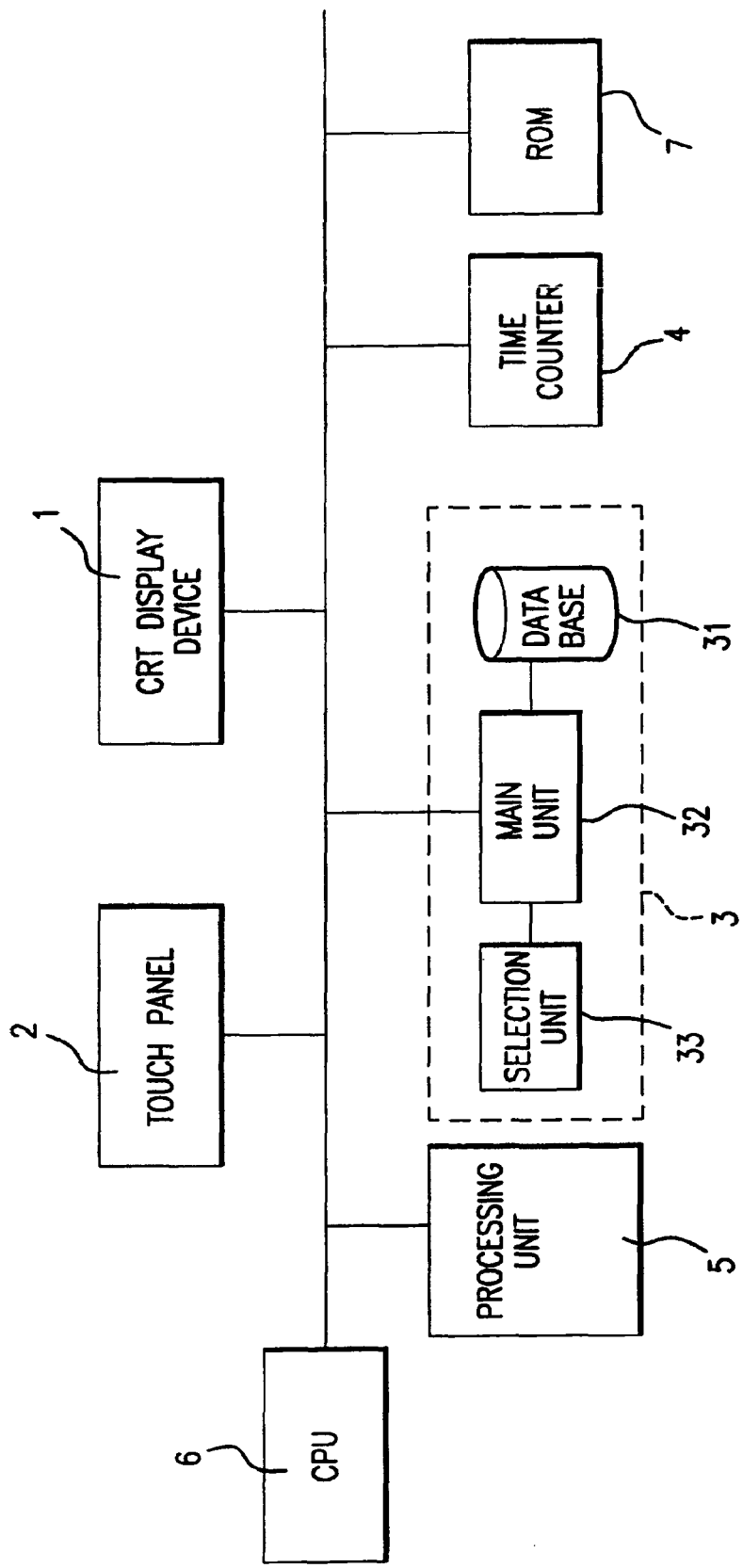
FIG. 1 shows a construction diagram of the apparatus according to the present invention.

As shown in the construction diagram in FIG. 1, the mentation test apparatus in an embodiment according to the present invention comprises: a display device 1 for displaying an image by electronic control; a transparent touch panel 2 overlaid on the screen of the display device 1; an image control device 3 for randomly distributing and displaying a given number of targets to be pointed in a prescribed order on the screen by controlling the display device 1, and for erasing a target pointed in a prescribed order by allowing a test subject point the target by pressing the position corresponding to the target on the touch panel in a prescribed order; a time counter 4 for measuring the search response time required for the test subject to search the targets in a correct order, and or the search response time required for the test subject to search a given number of the targets having a sequential order; a processing unit 5 for calculating the test subject's mentation based on the search response time measured with the time counter 4; and CPU 6 and ROM 7 for controlling these devices.

For example, a 17 inch CRT display device is used for the display device 1. A number of switching elements comprising a transparent electrode are aligned into a matrix in the touch panel 2 as known in the art, and the switch panel at the position corresponding to a target is turned on when the target displayed on the display device 1 is pressed from over the touch panel to input the coordinate of the display position of the target into the image control device 3.

The image control device 3 comprises a data base 31 storing an initial screen table for recording the coordinates, colors, shapes and sizes of 25 targets to be displayed on the screen (the initial screen), a main unit 32 for controlling the display device 1 based on the data read from the data base 31 or the data transferred from the touch panel 2, and a selection unit 33 to be described hereinafter.

A screen table having different dispositions of the targets and dummy targets after the targets have been pointed, for example a table filled with the data of 24 sorts of emergence patterns, are stored in the data base 31, in addition to the initial screen table. The colors, shapes and sizes of the dummy targets are also stored in the data base 31.

Figure 2:
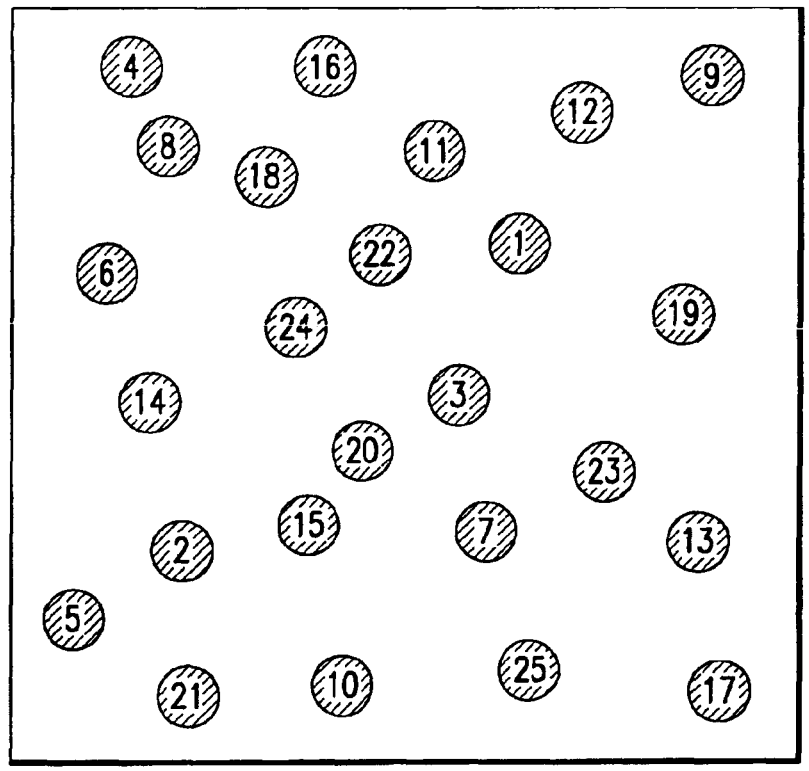
FIG. 2 shows an emergency pattern of the targets on the initial screen according to the present invention.

The main unit 32 is waiting for the test subject to point the first target, after reading the initial screen table from the data base 31 and randomly distributing and displaying 25 targets on the screen of the display device 1. As shown in the pattern diagram in FIG. 2, the background of the screen is colored to pale bluish gray, and each target is displayed as a black circular button with an appropriate size in which a mark comprising a figure indicating the order of pointing is displayed as a white contrast in the gray background.

The main unit 32 allows the display position of the target to be fixed and displayed until all the targets have been sequentially pointed. Also, the main unit comprises a function for displaying a dummy target having a different color from the pointed target in place of the pointed target, a function for fixing the display position and displaying the target until all the targets have been pointed, besides displaying a dummy target at random positions in place of the pointed target, and a function for displaying the remaining targets by changing their positions every time when a target has been pointed. Any one of these functions is selected and effectively used by the selection unit 33.

Figure 3:
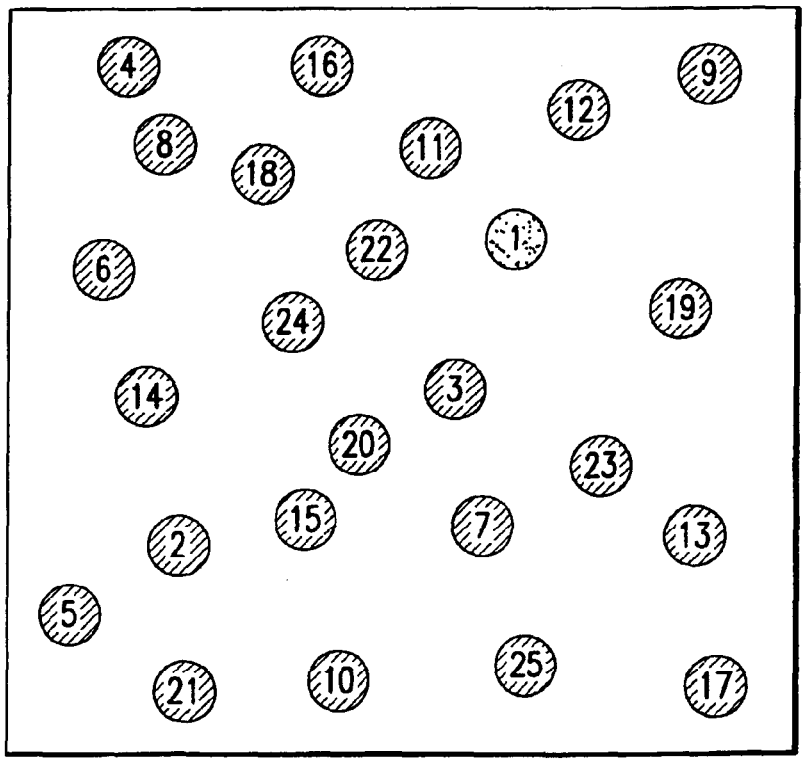
FIG. 3 shows an emergency pattern of the targets in test 1 according to the present invention.

For example, suppose the coordinate of the first target is imputed from the touch panel 2 when the first function is selected with the selection unit 33. Then, display of the target at the input position is halted as shown in the pattern diagram in FIG. 3, and a dummy target read from the data base is displayed at the corresponding position in place of the target.

While the dummy target is displayed as a circular button with the same shape and size as the target and with a figure indicating the pointing order displayed as a white contrast, the color of the dummy target is changed to orange color.

Figure 4:
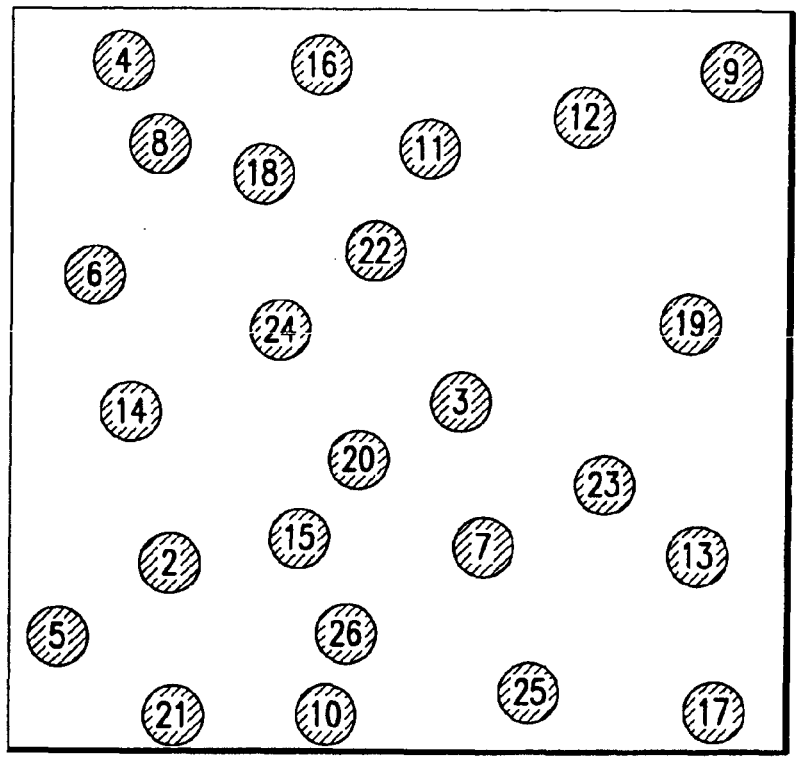
FIG. 4 shows an emergency pattern of the targets in test 2 according to the present invention.

Suppose the coordinate of the first target is imputed from the touch panel 2 when the second function is selected with the selection unit 33. Then, display of the target at the input position is halted as shown in the pattern diagram in FIG. 4, instead a dummy target read from the data base is displayed at the corresponding position of the erased target.

The dummy target configured as a black circular button with the same shape and size as those of the target, and a figure that has not been displayed, for example "26" when the first target is pointed or "27" when the second target is pointed, is displayed as a white contrast.

Figure 5:
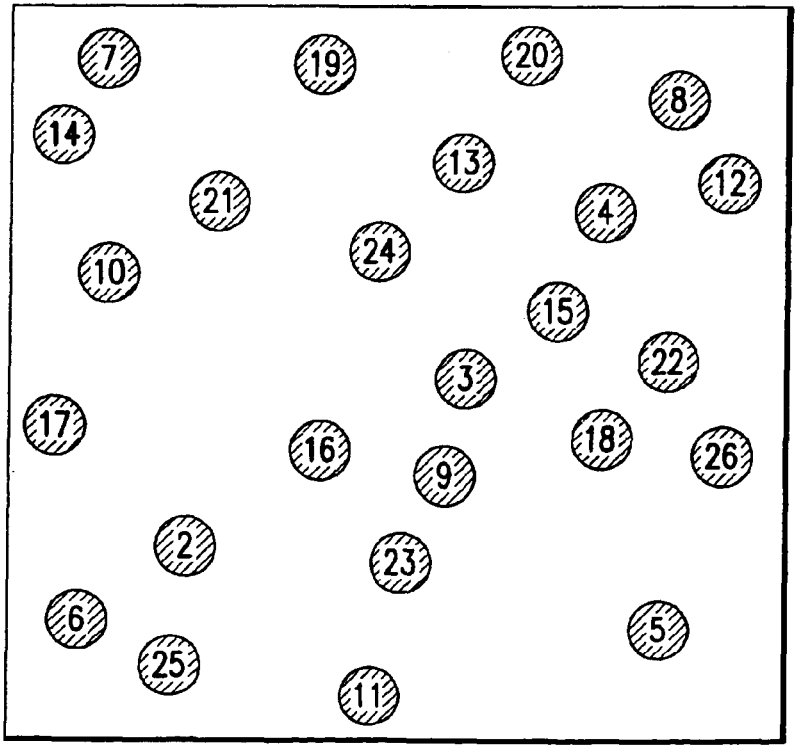
FIG. 5 shows an emergency pattern of the targets in test 3 according to the present invention.

Suppose the coordinate of the first target is imputed from the touch panel 2 when the third function is selected with the selection unit 33. Then, display of the target at the input position is halted as shown in the pattern diagram in FIG. 5, and a dummy target read from the data base is displayed in place of the target.

The display image table of the modified display positions of the targets and dummy targets after, for example, the first target has been pointed is read from the data base in this case, and the targets and dummy targets are randomly rearranged and displayed in accordance with the data.

A figure that has not been displayed is displayed as a white contrast in this black circular dummy target with the same shape and size as those of the target, as in the second function.

The order for selecting these functions is not particularly restricted, and the selection may be switched either manually or automatically.

The mentation test method in an embodiment according to the present invention is carried out using, for example, the mentation test apparatus as described above.

The test is executed in the order of the test 1 in which a given number of the targets to be pointed in a prescribed order are displayed on the screen of the display device by being randomly distributed, the test subject is made to point each target in a prescribed order, and a dummy target having a different color from the pointed target is displayed at the position of the pointed target in place of the pointed target when the target has been pointed in a correct order; the test 2 in which a given number of the targets to be pointed in a prescribed order are displayed on the screen of the display device by being randomly distributed, the test subject is made to point each target in a prescribed order, and a dummy target is displayed at random positions in place of the pointed target when the target has been pointed in a correct order; and the test 3 in which a given number of the targets to be pointed in a prescribed order are displayed on the screen of the display device by being randomly distributed, the test subject is made to point each target in a prescribed order, and a dummy target is displayed at random positions in place of the pointed target while changing the display positions of each target and dummy target when the target has been pointed in a correct order.

The time required for the test subject to search and point each target in each test is measured with the time counter 4.

The measurements were carried out with respect to normal adults of 40 males and 44 females with the age 18 or more and age 75 or less (mean age 43.2±17.0, S.D±1), respectively, as shown in Table 1. The mean search response times for the test 1 (task A), test 2 (task B) and test 3 (task C) were determined.

TABLE 1

Age Distribution of Normal Adults

| AGE | MALE | FEMALE | TOTAL |
|---|---|---|---|
| 18 to 19 | 1 | 4 | 5 |
| 20 to 29 | 9 | 8 | 17 |
| 30 to 39 | 6 | 9 | 15 |
| 40 to 49 | 9 | 5 | 14 |
| 50 to 59 | 6 | 10 | 16 |
| 60 to 69 | 8 | 5 | 13 |
| 70 to 79 | 1 | 3 | 4 |
| TOTAL | 40 | 44 | 84 |

Figure 6:
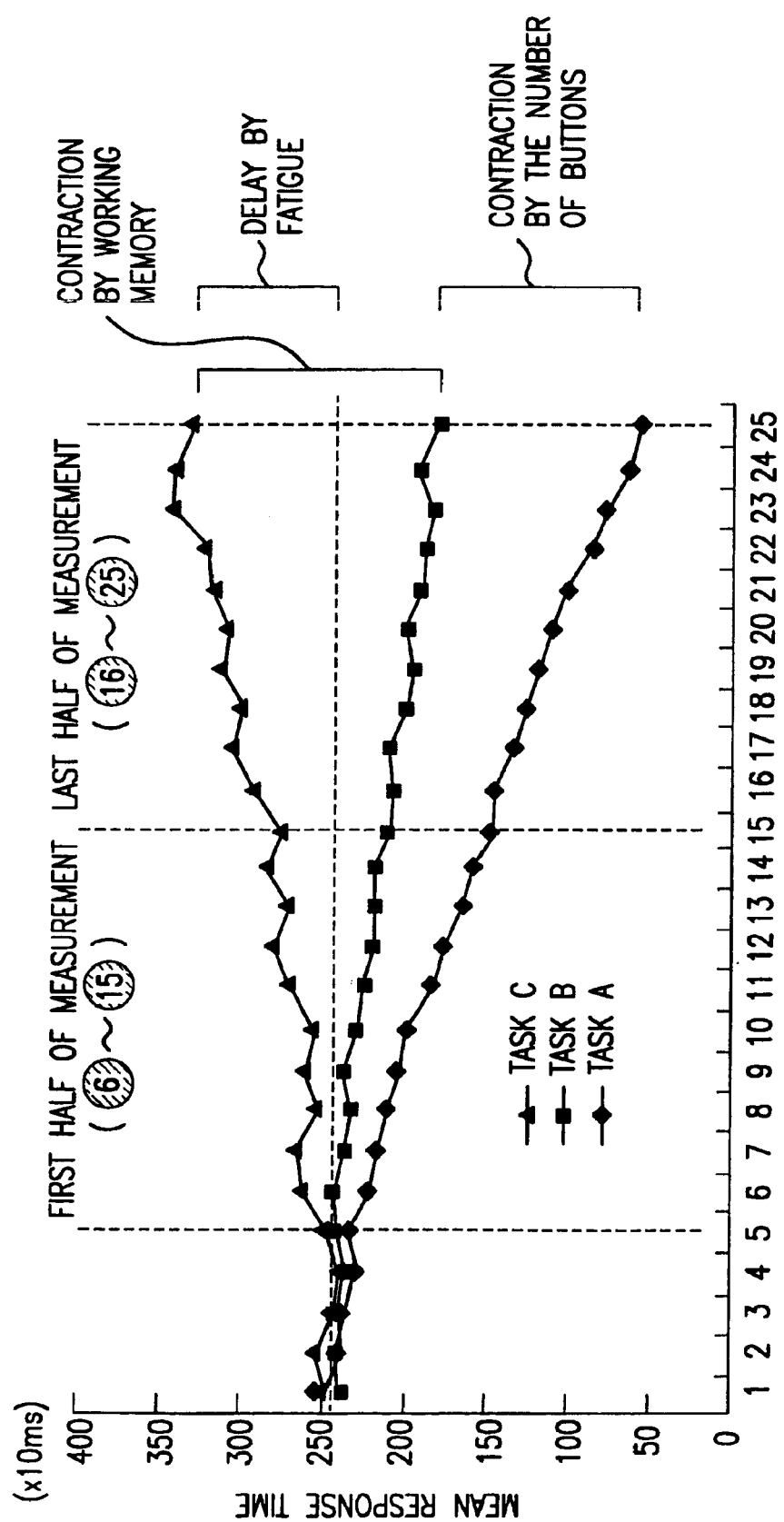
FIG. 6 shows a two dimensional dispersion analysis diagram of the mean search response time of each target according to the present invention.
Figure 7:
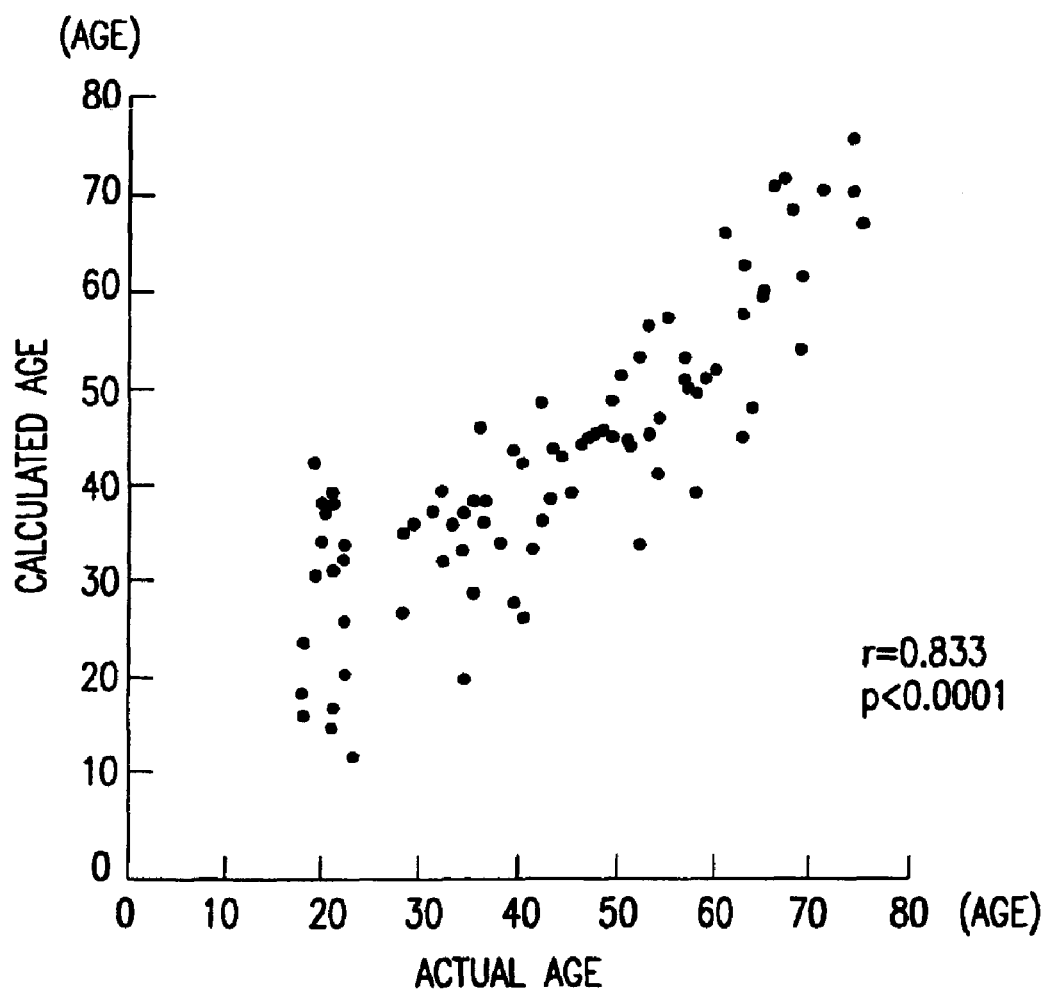
FIG. 7 shows a two dimensional dispersion analysis diagram of the calculated age and actual age according to the present invention.

For example, the mean search response time of 14 normal adults (nine males and five females) in their forties for each target was 2400 to 2550 ms from the first through the fifth targets as shown in the two dimensional analysis of variance in FIG. 6, showing no evident difference among the tests. However, the mean search response time was delayed in the test 3 (task C) and contracted in the test 1 and test 2.

In the test 3 (task C), the dispositions of all the targets and dummy targets change every time when the targets have been pointed. Since the total number of the targets and dummy targets is unchanged, delay in the search response time seems to be caused by fatigue.

Since the positions of the target once appeared and of the dummy targets are unchanged in the test 2 (task B), search of a target and memory of the display positions of the other targets and dummy targets are processed in parallel. Accordingly, the score in the test 2 (task B) is contracted relative to the score in the test 3 (task C) due to operation of the working memory.

A remarkable contraction is observed in the test 1 (task A) as compared with the test 2 (task B). This is because the search area is limited to the targets that have not been pointed yet by changing the color of the dummy targets to the orange color that is different from the black color of the targets, besides the number of the targets that has not been pointed is decreased, or the number of the buttons is decreased.

After the similar tests carried out for each age range, the search response times for the first to fifth targets were omitted from the analysis considering the effects of tension and inexperience. Among the sixth to $25^{th}$ targets, the sixth to $15^{th}$ targets were classified as the first half targets and the $16^{th}$ to $25^{th}$ targets were classified as the last half targets.

As shown in Table 2, the mean search response time was prolonged in all the tests as the ages of the test subjects are higher, showing delay by aging. The results are more closely related to the age than the results in the one-digit addition task (simplified task in Uchida-Kraepelin's test) do, and a quite strong correlation with the age were observed particularly in the last half of the test 2 (task B) and in the last half of the test 3 (task C).

TABLE 2

SEARCH RESPONSE TIME (ms/target) PER ONE TARGET OBSERVED IN EACH AGE RANGE OF NORMAL ADULTS, AND RESULTS OF ONE-DIGIT ADDITION TASK

| AGE | n | TASK A FIRST HALF | TASK A LAST HALF | TASK B FIRST HALF | TASK B LAST HALF | TASK C FIRST HALF | TASK C LAST HALF | ONE-DIGIT ADDITION TASK (CORRECT ANSWERS/ 3 MIN) |
|---|---|---|---|---|---|---|---|---|
| 18–19 | 5 | 1480 ± 345 | 975 ± 251 | 2118 ± 458 | 1755 ± 295 | 2391 ± 432 | 2619 ± 600 | 181.8 ± 26.1 |
| 20–29 | 17 | 1465 ± 272 | 864 ± 169 | 2076 ± 391 | 1810 ± 195 | 2189 ± 290 | 2672 ± 349 | 164.5 ± 20.5 |
| 30–39 | 15 | 1590 ± 217 | 924 ± 79 | 2282 ± 412 | 1990 ± 303 | 2389 ± 369 | 2900 ± 398 | 163.0 ± 26.4 |
| 40–49 | 14 | 1769 ± 237 | 1045 ± 173 | 2467 ± 345 | 2215 ± 346 | 2669 ± 317 | 3254 ± 497 | 139.4 ± 19.6 |
| 50–59 | 16 | 1989 ± 294 | 1321 ± 239 | 2671 ± 368 | 2383 ± 390 | 2782 ± 322 | 3683 ± 441 | 132.5 ± 28.1 |
| 60–69 | 13 | 2636 ± 377 | 1576 ± 331 | 3051 ± 364 | 3001 ± 617 | 3115 ± 400 | 3970 ± 617 | 114.1 ± 31.2 |
| 70–74 | 4 | 35961 ± 573 | 2340 ± 240 | 3594 ± 369 | 3683 ± 418 | 4000 ± 389 | 4766 ± 540 | 101.8 ± 26.7 |
| CORRELATION WITH AGE | | 0.75*** | 0.75*** | 0.75*** | 0.77*** | 0.72*** | 0.76*** | 0.63*** |

Pearson test: ***p < 0.001

The search response time for each target in each test was summarized in the fast half and last half of the test, respectively. The ratios (task A) between the fast half and last half (last half/first half) in the test 1 (task A), and between the first half and last half (last half/first half) in the test 3 (task C), and the ratio of the last half of the test 2 (task B) relative to the last half of the test 3 (task C) were determined. As shown in Table 3, the search response time in the last half of the test was more contracted than that in the first half of the test in any generation with respect to the ratio between the last half and first half in the task A, showing no correlation with the age.

TABLE 3

PARAMETERS ON THE TIME PERIOD REQUIRED FOR COMPLETING THE TASK IN EACH GENERATION OF NORMAL ADULT

| AGE | n | RATIO BETWEEN FIRST HALF AND LAST HALF IN TEST 1 (TASK A) LAST HALF/ FIRST HALF | RATIO BETWEEN FIRST HALF AND LAST HALF IN TEST 3 (TASK C) LAST HALF/ FIRST HALF DEGREE OF DELAY BY FATIGUE | RATIO OF LAST HALF OF TEST 3 (TASK C) RELATIVE TO LAST HALF TEST 2 (TASK B) LAST HALF OF TASK B/ LAST HALF OF TASK C DEGREE OF CONTRACTION BY WORKING MEMORY |
|---|---|---|---|---|
| 18–19 | 5 | 0.66 ± 0.07 | 1.08 ± 0.10 | 0.68 ± 0.08 |
| 20–29 | 17 | 0.60 ± 0.11 | 1.22 ± 0.08 | 0.69 ± 0.10 |
| 30–39 | 15 | 0.60 ± 0.11 | 1.25 ± 0.07 | 0.67 ± 0.07 |
| 40–49 | 14 | 0.60 ± 0.11 | 1.22 ± 0.07 | 0.68 ± 0.08 |
| 50–59 | 16 | 0.67 ± 0.13 | 1.33 ± 0.14 | 0.65 ± 0.08 |
| 60–69 | 13 | 0.60 ± 0.08 | 1.27 ± 0.10 | 0.75 ± 0.07 |
| 70–74 | 4 | 0.66 ± 0.05 | 1.19 ± 0.14 | 0.77 ± 0.06 |
| CORRELATION WITH AGE | | n. s. | 0.27* | 0.24* |

Spearman test: *p < 0.05

In the test 3 (task C), the search response time was more delayed in the last half than in the first half with a slight correlation with the age, showing that the effect of fatigue was larger in the aged.

Since contraction of the search response time in the last half of the test 2 (task B) relative to the last half of the test 3 (task C) is conjectured to be caused by permitting the working memory to operate, a correlation with the age that the working memory dulls in the higher age was observed.

Since correlation of each search response time in the first half and last half of the test 1 (task A), in the first half and last half of the test 2 (task B) and in the first half and last half of the test 3 (task C) with aging was observed, the following equations 1 and 2 were obtained from a step-wise regression analysis with additional correction of curve.

Equation 1:

$$X = 0.0154 \times (\text{first half of task } A) + 0.00978 \times (\text{last half of task } C) - 0.005535 \times (\text{first half of task } C) + 0.003645 \times \times (\text{last half of task } B) - 3.681 (\text{distinction of sex}) - 6.612,$$

wherein the term "distinction of sex" is substituted with 1 or 2 in male and female, respectively.

Equation 2:

$$\text{ATMT calculated age } (Y) = -0.0091X^2 + 1.8771X - 19.192$$

As shown in the two dimensional dispersion analysis diagram with respect to the correlation between the calculated age and actual age, the mentation age of the test subject's brain calculated as described above is highly reliable, since the calculated age is closely approximated with the actual age in the age thirties or more, although a slight distribution is observed in the age twenties.

Similarly, the test 1, test 2 and test 3 were applied to 17 normal adults with the age sixty or more (nine males and eight females, mean age 66.9±4.6), and to 14 patients with mild senile dementia and boundary senile dementia (eight males and six females, mean age 68.6±3.3) who visited the senile internal medicine clinic.

The patients with mild senile dementia and boundary senile dementia (referred as early dementia patients hereinafter) were restricted to those who have experienced at least two times of episodes skeptical of symptoms of dementia and showing a Hasegawa's dementia scale of 22 or more and 27 or less.

The test subjects were divided into two groups of the normal adults and early dementia patients, and the mean search response times in the first half and last half of each test in each group were determined by the same method as described above. The results are shown in Table 4.

the ratio between the first half and last half (last half/first half) of the test 1 (task A), no difference was observed in the ratio between the first half and last half (last half/first half) of the test 3 (task C) that is thought to indicate the degree of delay by fatigue.

The ratio of the last half of the test 2 (task B) relative to the last half of the test 3 (task C) is conjectured to indicate the extent of application of the working memory, and a significant difference was observed between the normal adults and early dementia patients.

To verify the difference between the normal adults and early dementia patients, the ratios (the degree of contraction) of the last half of the test 2 (task B) relative to the last half of the test 3 (task C) for the 84 normal adults with their age in the range of 18 to 74, and those of the early dementia

TABLE 4

COMPARISON OF NORMAL ADULTS AND DEMENTIA PATIENTS AT AGE 60 OR MORE

| | | TASK A | | TASK B | | TASK C | | ONE DIGIT ADDITION TASK (CORRECT |
|---|---|---|---|---|---|---|---|---|
| | n | FIRST HALF | LAST HALF | FIRST HALF | LAST HALF | FIRST HALF | LAST HALF | ANSWER/3 MIN) |
| NORMAL | 17 | 2853 ± 575 | 1756 ± 452 | 3178 ± 362 | 3161 ± 638 | 3323 ± 545 | 4157 ± 745 | 111.2 ± 28.9 |
| DEMENTIA | 14 | 3697 ± 522 | 1949 ± 524 | 3891 ± 369 | 4788 ± 1103 | 3963 ± 571 | 4923 ± 872 | 69.7 ± 16.4 |
| SIGNIFICANT DIFFERENGE BETWEEN TWO GROUPS | | $P < 0.001$ | $P < 0.001$ | $P < 0.01$ | $P < 0.001$ | $P < 0.01$ | $P < 0.01$ | $P < 0.001$ | t test

The test subjects were also divided into two groups of the normal adults and early dementia patients, and the ratios between the first half and last half (last half/first half) in the test 1 (task A), and between the first half and last half (last half/first half) in the test 3 (task C), and the ratio of the last half of the test 2 (task B) relative to the last half of the test 3 (task C) were determined. The results are shown in Table 5.

TABLE 5

COMPARISON OF PARAMETERS ON THE TIME PERIOD REQUIRED FOR COMPLETING THE TASK IN NORMAL ADULTS AND DEMENTIA PATIENTS AT AGE 60 OR MORE

| | n | RATIO BETWEEN FIRST HALF AND LAST HALF IN TASK A LAST HALF/ FIRST HALF | RATIO BETWEEN FIRST HALF AND LAST HALF IN TASK C LAST HALF/ FIRST HALF DEGREE OF DELAY BY FATIGUE | RATIO OF LAST HALF OF TEST B RELATIVE TO LAST HALF OF TEST C LAST HALF OF TASK B/ LAST HALF OF TASK C DEGREE OF CONTRACTION BY WORKING MEMORY |
|---|---|---|---|---|
| NORMAL | 17 | 0.61 ± 0.08 | 125 ± 0.11 | 0.76 ± 0.07 |
| DEMENTIA | 14 | 0.79 ± 0.08 | 124 ± 0.11 | 0.96 ± 0.93 |
| SIGNIFICANT DIFFERENCE BETWEEN TWO GROUPS | | $p < 0.001$ | n. s. | $p < 0.001$ |

Mann-Whitney test

Figure 8:
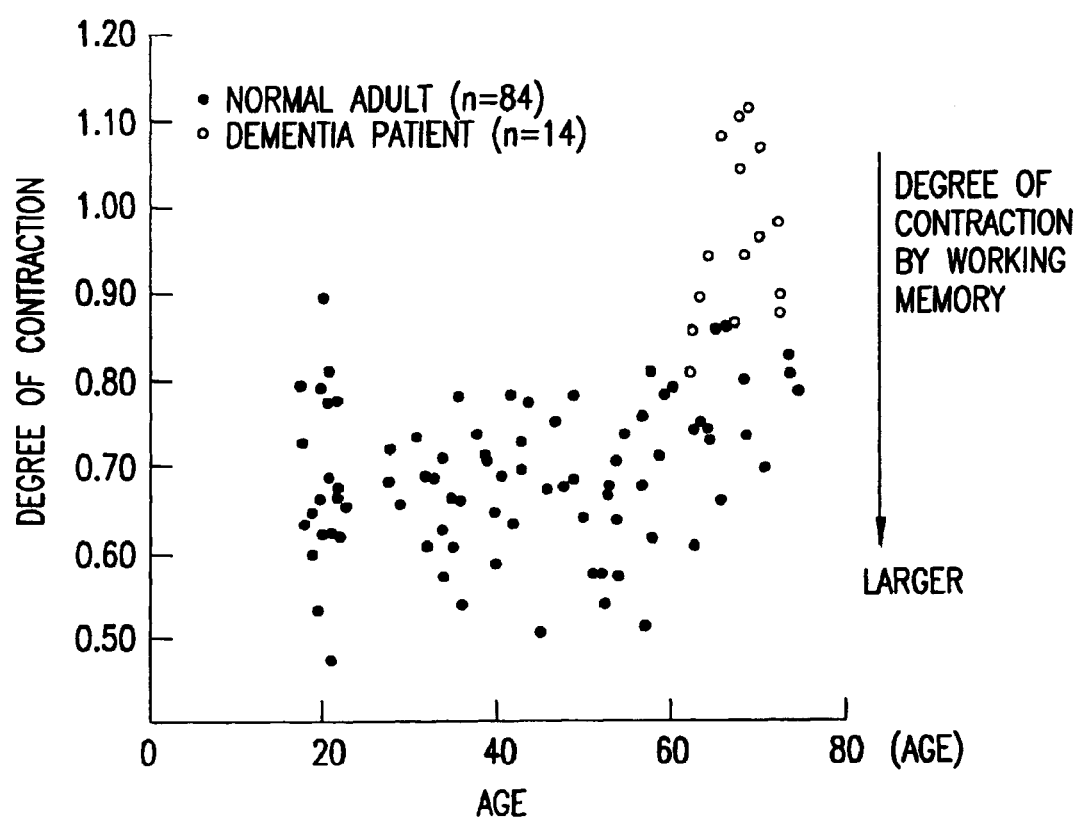
FIG. 8 shows a two dimensional dispersion analysis diagram of the degree of contraction and age according to the present invention.

Table 5 shows that, while significant differences were observed between the normal adults and dementia patients in patients were filled in the two dimensional dispersion analysis diagram shown in FIG. 8. It was revealed that the values of the early dementia patients were completely distributed in the range of 0.85 or more, in contrast to the distribution of the normal adults of less than 0.85 with few exceptions of three subjects in total of 84 subjects.

According to the mentation test method, the early dementia patients can be detected with a detection ratio of 100% including 0% of pseudo-negative ratio and 3.5% of pseudo-positive ratio, by calculating the ratio of the last half of the test 2 (task B) relative to the last half of the test 3 (task C) and deciding whether the ratio is 0.85 or more or less than 0.85.

The search response time is measured for each target, and the display position of the target is stored as a coordinate in the data base. Consequently, testing of dominance of the cerebral hemisphere and visual field disorders such as constriction of peripheral attention visual field is possible based on the positional coordinates (vector) of the pointed targets and search response time in the test 3 (task C) in which the positional coordinates are changed every time when the targets have been pointed.

The test method can be also applied for testing the degree of mental function due to drinking and medication, or for testing the degree of drinking, medication dose and side effect of medicines.

With respect to the effect of intake of alcohol on the test results, a significant decrease of the test score can be detected in the test subject who has exhibited no effect of alcohol on his sense of equilibrium and behavior. A significant improvement of the test achievement after intake of caffeine can be also detected, showing the ability of the test for quite sensitively detecting the mentation of the brain.

The test subject can enjoy the mentation test of the brain as if he (or her) is playing a game, because the test subject is able to learn his (her) mentation age of the brain at the test site when the calculated mentation age of the test subject's brain is displayed on the screen of the display device 1 after completing the entire tests.

When the apparatus according to the present invention is installed, for example, in the waiting room of a hospital, visitors of the hospital would be interested in finding early onset of dementia or in the probability of onset of dementia to make them easy to voluntarily receive the mentation test. This will enable onset of dementia to be found in its early stage, or probability of onset of dementia to be informed, thereby giving an opportunity to be alert on onset of dementia, or to take preventive measures against onset of dementia.

In the method according to the present invention, a given number of the targets to be pointed in a prescribed order is randomly distributed and displayed on the screen of the display device, the search response time required for the test subject to search each target is measured by requesting the test subject to point each target in a prescribed order, and the mentation of the test subject is calculated based on the measured values. Accordingly, the mentation age of the brain can be conjectured, and onset of early dementia and the probability of onset of dementia can be diagnosed, besides enabling the degree of drinking, the effects of medication and side effects of medication, the effects of rehabilitation of cerebrovascular disorder, dominance of cerebral hemisphere and peripheral attention visual field to be sensitively discriminated.

A highly reliable mentation test is possible without any correlation with educational carrier as seen in the Uchida-Kraepelin's dementia scale, or without being affected by the effects of repeated learning as seen in the Hasegawa's dementia scale.

It is possible to repeatedly apply the mentation test within a short period of time because no effects of the repeated learning are observed, enabling the test to be quite favorably applied for the action of medicines and side effects of medicines, decision of the effects of rehabilitation of cerebrovascular disorder, and decision of the effects of medicines.

Further, the test is promptly carried out by electronic control to rapidly display the calculated results, for example the test results are displayed on the screen in place of the targets that have been displayed. Accordingly, the test subject can enjoy the test as if he (or she) is playing a game, visitors of the hospital would be interested in finding early onset of dementia or in the probability of onset of dementia to make them easy to voluntarily receive the mentation test by installing the apparatus in, for example, the waiting room of a hospital.

The apparatus according to the present invention comprises a display device for displaying the image by electronic control, a transparent touch panel overlaid on the screen of the display device, an image control device for randomly distributing and displaying a given number of the targets to be pointed in a prescribed order by controlling the display device, and for erasing the targets that have been pointed in a correct order when the test subject presses the position corresponding to each target on the touch panel in a prescribed order to point the target, a time counter for measuring the search response time required for the test subject to search the target in a correct order, and/or the search response time required for the test subject to search a given number of the continuous targets, and a processing device for calculating the mentation of the test subject based on the search response time measured by the time counter. Consequently, it is possible to apply the method according to the present invention by which a given number of the targets to be pointed in a prescribed order are randomly distributed and displayed on the screen of the display device, the search response time required for the test subject to search each target is measured by allowing the test subject to point each target in a prescribed order and mentation of the test subject is calculated based on the measured values.

The mentation age of the brain can be conjectured, and presence of early onset dementia and prediction probability of onset of dementia can be accurately diagnosed, besides enabling the degree of drinking, the effects of medicines and side effect of medicines, and rehabilitation effects of cerebrovascular disorder to be sensitively and accurately decided with repetition within a short period of time.

When the apparatus according to the present invention is installed, for example, in the waiting room of a hospital, visitors of the hospital would be interested in finding early onset of dementia or in the probability of onset of dementia to make them easy to voluntarily receive the mentation test.

We claim:

1. A mentation test apparatus comprising:
   a display means for displaying images by electronic control;
   a transparent touch panel overlaid on a screen of the display means;
   an image control means for randomly disposing and displaying a given number of targets to be pointed to in a prescribed order on the screen by controlling the display means, and for erasing the targets that have been pointed to in a correct order when a test subject points to the targets by pressing a position corresponding to each target on the touch panel in a prescribed order;
   a time counter for measuring a search response time required by the test subject for searching each of the targets in a correct order and the search response time required by the test subject for searching the given number of targets in correct sequential order, and a processing means for calculating the mentation of the test subject based on the search response times measured by the time counter and the sequential order.

2. The mentation test apparatus according to claim 1, wherein the image control means comprises a function for controlling the display means to display dummy targets at the positions where the targets have been erased or at random positions in place of the targets that have been erased.

3. The mentation test apparatus according to claim 2, wherein the image control means comprises a function for controlling the display means to display the dummy targets being different in at least one of the color, shape and size in place of the targets that have been erased.

4. The mentation test apparatus according to any one of claims 1 to 3, wherein the image control means comprises a function for controlling the display means to display marks indicating the sequential order of pointing as the targets or in addition to the targets, and for controlling the display means to display marks other than the marks that have been already displayed as dummy targets in place of the erased targets.

5. The mentation test apparatus according to any one of claims 1 to 3 wherein the image control means comprises a function for controlling the display means to display each target that has not been pointed to yet by changing a display position of the target every time the other targets have been pointed in a correct order.

6. The mentation test apparatus according to claim 1 comprising:
an image control means for executing, in a prescribed order,
a test 1 in which a given number of the targets to be pointed in a prescribed order are displayed on the screen of the display means by being randomly distributed, the test subject is requested to point each target in a prescribed order, and a dummy target having a different color from the target is displayed in place of the pointed target at the position of the pointed target when the target is pointed in a correct order;
a test 2 by controlling the display means to erase a target from the screen when the target is pointed in a correct order, and to display a dummy target on the screen at random positions in place of the target that has been erased, and
a test 3 by controlling the display means to erase a target from the screen when the target is pointed in a correct order, and to display a dummy target at random positions on the screen in place of the target that has been erased, while controlling the display means to display each target and dummy target by changing their display positions;
a processing means for calculating the degree of contraction of the search response time by a working memory for parallel processing of search and memory of positions based on the search response time of each target measured by the time counter in each test; and
a diagnosis means for diagnosing presence of dementia or prediction probability of onset of dementia based on the calculation results.

7. The mentation test apparatus according to claim 6, wherein the image control means allows the display means to display the search response time for each target in each test measured by the time counter after completing the entire test.

8. The mentation test apparatus according to claim 6 or 7, wherein the image control means allows the display means to display the results of diagnosis by the diagnosis means after completing the entire test.

9. The mentation test apparatus according to claim 1 further comprising a printer for printing test results.

10. A mentation test apparatus comprising:
a display means for displaying images by electronic control;
a transparent touch panel overlaid on a screen of the display means;
an image control means for randomly disposing and displaying a given number of targets to be pointed to in a prescribed order on the screen by controlling the display means, and for erasing the targets that have been pointed to in a correct order when a test subject points to the targets by pressing a position corresponding to each target on the touch panel in a prescribed order; and
a time counter for measuring a search response time required by the test subject for searching each of the targets in a correct order and the search response time required by the test subject for searching the given number of targets in correct sequential order, and a processing means for calculating the mentation of the test subject based on the search response times measured by the time counter;
wherein the image control means includes:
a function for controlling the display means to erase a target from the screen when the target is pointed in a correct order, and to display a dummy target having a different color at the position of the target in place of the target that has been erased;
a function for controlling the display means to erase a target from the screen when the target is pointed in a correct order, and to display a dummy target at random positions in place of the target that has been erased;
a function for controlling the display means to erase a target from the screen when the target has been pointed in a correct order, and to display a dummy target at random positions in place of the target that has been erased, while controlling the display means to display each target and dummy target by changing their display positions; and
a selection means for making any one of the functions effective, wherein the mentation age of the test subject's brain is calculated by the processing means based on the search response time measured by the time counter in a test using each function.

* * * * *